United States Patent
Schüller

(10) Patent No.: US 7,177,687 B2
(45) Date of Patent: Feb. 13, 2007

(54) IMPLANTABLE CARDIAC STIMULATOR WHEREIN AV-DELAY ADJUSTMENT IS LIMITED DURING DYNAMIC ATRIAL OVERDRIVE

(75) Inventor: Hans Schüller, Lund (SE)

(73) Assignee: St. Jude Medical AB (SE)

( * ) Notice: Subject to any disclaimer, the term of this patent is extended or adjusted under 35 U.S.C. 154(b) by 0 days.

(21) Appl. No.: 10/272,850

(22) Filed: Oct. 16, 2002

(65) Prior Publication Data

US 2003/0114890 A1 Jun. 19, 2003

(30) Foreign Application Priority Data

Dec. 18, 2001 (SE) .................................... 0104296

(51) Int. Cl.
*A61N 1/368* (2006.01)
(52) U.S. Cl. ............................................ 607/25; 607/9
(58) Field of Classification Search ................. 607/9, 607/14, 15, 25
See application file for complete search history.

(56) References Cited

U.S. PATENT DOCUMENTS

| 4,503,857 | A |   | 3/1985 | Boute et al. |       |
|-----------|---|---|--------|--------------|-------|
| 4,554,921 | A | * | 11/1985 | Boute et al. | 607/9 |
| 4,856,524 | A |   | 8/1989 | Baker, Jr. |       |
| 5,330,511 | A |   | 7/1994 | Boute |       |
| 6,058,328 | A |   | 5/2000 | Levine et al. |       |
| 6,081,747 | A |   | 6/2000 | Levine et al. |       |

FOREIGN PATENT DOCUMENTS

| EP | 0 450 487 | 10/1991 |
| EP | 0 607 951 | 7/1994 |
| EP | 1 110 580 | 6/2001 |

OTHER PUBLICATIONS

"Use of Flywheel, Automatic Underdrive and Dynamic Overdrive in Atrial Pacers," Barnay et al., "Cardiac Pacemakers: Diagnostic Options, Dual Chamber Pacing, Rate Responsive Pacing, Antitachycardia Pacing," (1985) pp. 238-247.

* cited by examiner

*Primary Examiner*—George Manuel
*Assistant Examiner*—Nicole R. Kramer
(74) *Attorney, Agent, or Firm*—Schiff Hardin LLP

(57) ABSTRACT

A cardiac pacemaker has an algorithm for dynamic overdrive of a patient's atria in order to suppress atrial tachyarrhythmias. The device further has circuitry for adapting the AV-delay during dynamic overdrive of the atria to a value adapted to the patient's needs.

8 Claims, 3 Drawing Sheets a) PV delay for sensed P-waves.
b) AV delay for atrial paced beats.
c) AV delay for atrial paced beats during atrial overdrive.

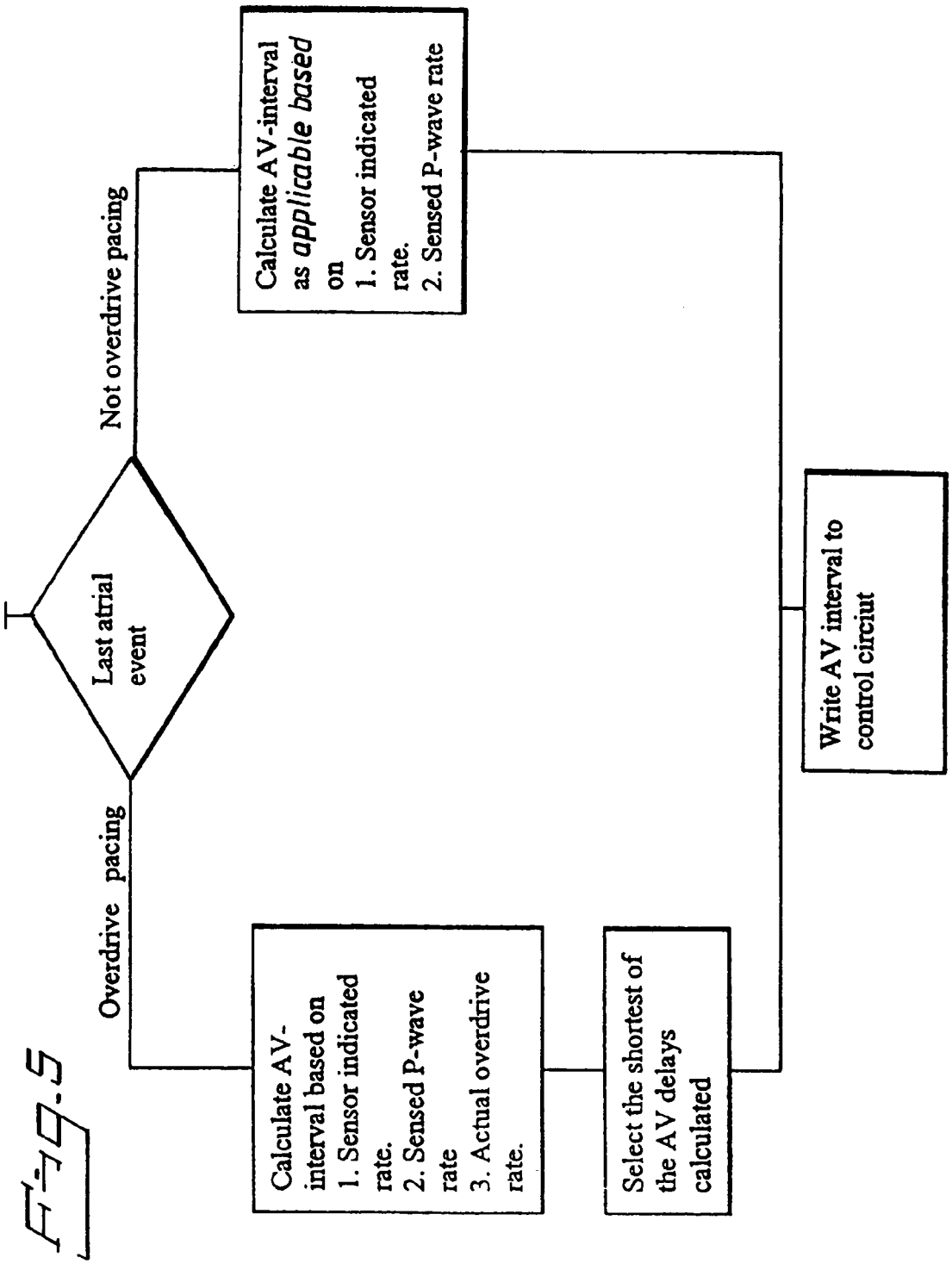

IMPLANTABLE CARDIAC STIMULATOR WHEREIN AV-DELAY ADJUSTMENT IS LIMITED DURING DYNAMIC ATRIAL OVERDRIVE

BACKGROUND OF THE INVENTION

1. Field of the Invention

The present invention relates to an implantable cardiac stimulating device of the type having the capability to adapt the AV-delay depending on different operating conditions of the cardiac stimulating device.

2. Description of the Prior Art

Under healthy heart conditions an exercise-induced increase in heart rate is followed by a shortening of the heart's physiologic P-R interval.

In pacemaker technology the term AV-delay is used for AV sequential pacing and the term PV-delay is used for sensed P-waves followed by ventricular stimulations synchronized to the sensed P-wave.

Hence, among the approaches to provide physiological pacing in modern DDD pulse generators, an algorithm for stimulation rate-correlated shortening of the AV/PV delay is used. While this is physiological during exercise and of benefit in DDD/VDD pacing at higher rates, the shortening is, as first understood by the inventor herein, less appropriate during periods of high stimulation rate at rest. This situation might occur during a situation referred to as atrial overdrive.

Atrial overdrive is used to suppress spontaneous atrial activity in patients who suffer from paroxysmal atrial tachyarrhythmias. Atrial overdrive might be implemented as dynamic overdrive which means that the pulse generator normally provides a stimulation rate that is slightly above the underlying, possibly varying, intrinsic rate.

One example of overdrive pacing is described in U.S. Pat. No. 4,503,857, which discloses the concept of dynamic overdrive in order to achieve a high percentage of pacing at a rate only slightly higher than the underlying intrinsic rate.

The article "Use of flywheel, Automatic underdrive and dynamic overdrive in atrial pacers" by C. Barnay and J. L. Medvedowski in the book "Cardiac pacemakers: Diagnostic options, dual chamber pacing, rate responsive pacing, anti-tachycardia pacing" provides a description of the concept of dynamic overdrive of the atria for the purpose of suppressing atrial tachyarrhythmias. The book is edited by Behrenbeck. D. W. and published by Darmstadt, Steinkopf, Springer Verlag, New York, 1985.

The algorithm disclosed in the two documents mentioned above for implementing dynamic overdrive is that if there has been an atrial inhibition the stimulation rate is increased with a predetermined step. This algorithm for increase of the stimulation rate is applied as long as there are atrial inhibitions. When 100% pacing is achieved after increasing the stimulation rate in one or several steps the pacing rate is slowly decreased until an atrial inhibition is detected in which case the stimulation rate is increased again by a predetermined step as described above. If the patient has arrhythmic tendencies such as frequent PAC's (Premature Atrial Contraction) this may result in a stimulating rate that is significantly higher than the optimal physiologic rate. If no inhibitions occur the pacemaker will stimulate at its base rate or lower rate. If the pacemaker is of the rate responsive type the pacemaker will operate at its sensor indicated rate. In the two last cases the pacemaker will overdrive the heart but it will not operate in dynamic overdrive.

None of the above documents, however, discloses anything regarding the problem with the AV-interval shortening during nonphysiological dynamic overdrive pacing for tachyarrhythmia suppression.

SUMMARY OF THE INVENTION

An object of the present invention is to provide automatic adjustment of the AV-delay under dynamic overdrive of the atrium.

This object is achieved by a cardiac pacemaker of the type described above wherein a control circuit adjusts the sensed and paced AV/PV delays to obtain physiologically optimal AV/PV delays at different paced and sensed heart rates, and wherein the control circuit operates the pacing circuitry to, under appropriate conditions, in a mode for dynamic overdrive of the atrium, and wherein the AV delay adjustment is limited if the device is in the dynamic atrial overdrive mode.

The present invention thus is concerned with a cardiac pacemaker which provides an AV-interval which is optimized for the heart under all conditions including dynamic overdrive of the atrium for atrial tachyarrhythmia suppression. The inventor has, as noted above, found that shortening of the AV-interval during dynamic atrial overdrive may be unphysiological and that such shortening should be limited or avoided.

In a preferred embodiment the AV-delay used during dynamic overdrive is the base rate or lower rate AV delay. The lower rate or base rate is the stimulation rate used by the pacemaker when the stimulation rate is not affected by sensed P-waves or by a sensor for rate responsiveness.

In another preferred embodiment the AV-delay used during dynamic overdrive of the atria is the AV delay indicated by the sensor rate.

In a third embodiment the AV-delay used during dynamic overdrive is the AV-delay indicated by the underlying intrinsic rate. This embodiment is particularly useful in patients in which the underlying physiologic rate can be determined with a good accuracy. The underlying physiologic rate can be determined from sensed P-waves or from a physiologic sensor. This is particularly advantageous if the pulse generator is adapted to employ well known techniques to differentiate PAC's from P-waves originating from the sinus node. One way to accomplish this differentiation is morphology analysis of the P-wave. Only P-waves originating from the sinus node shall be employed for determination of the underlying physiologic rate.

In a fourth embodiment the AV-delay used during dynamic overdrive is determined from several input factors. Examples of these input factors may be the physiologic underlying intrinsic rate, the sensor indicated rate, the actual overdrive rate. The determination may employ averaging or other weighting of the input factors.

In normal cases, such as when the pacemaker is tracking P-waves at elevated rates, the well known AV-interval shortening is available in order to provide the patient with an optimal cardiac rhythm. This mode of operation is, however, infrequent when dynamic overdrive of the atrium is active.

DESCRIPTION OF THE DRAWINGS

FIG. 5 shows one example of a flow chart for how the AV interval may be calculated.

DESCRIPTION OF THE PREFERRED EMBODIMENTS

Figure 1:
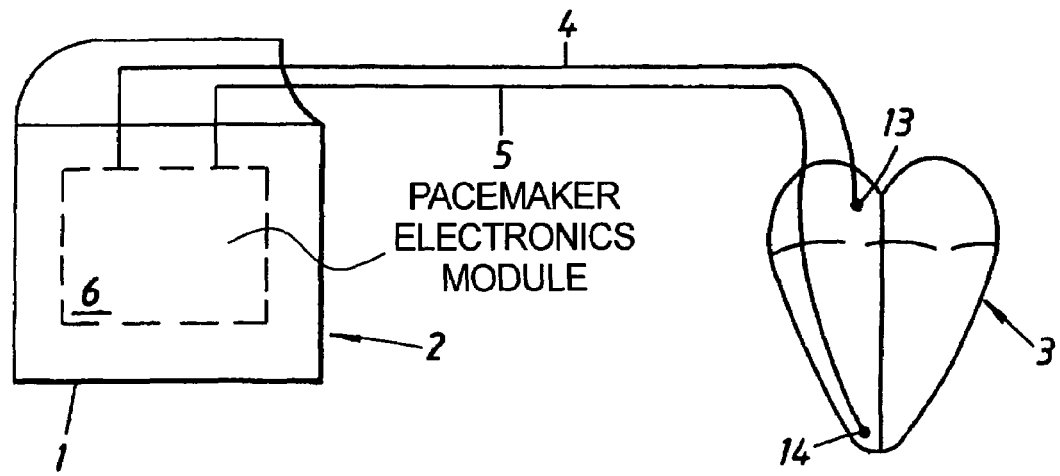
FIG. 1 shows a typical cardiac pacemaker connected to a patient's heart via leads.

FIG. 1 shows a typical cardiac pacemaker 1 with a pacemaker electronics module 6 inside a hermetically sealed enclosure 2. The cardiac leads 4 and 5 with attached electrodes 13 and 14 conduct stimulation pulses to the patient's heart 3. Signals originating from P-waves and R-waves are picked up by electrodes 13 and 14 and conducted by the leads 4 and 5 to the pacemaker electronics module 6 which includes circuitry for detection of those signals.

Figure 2:
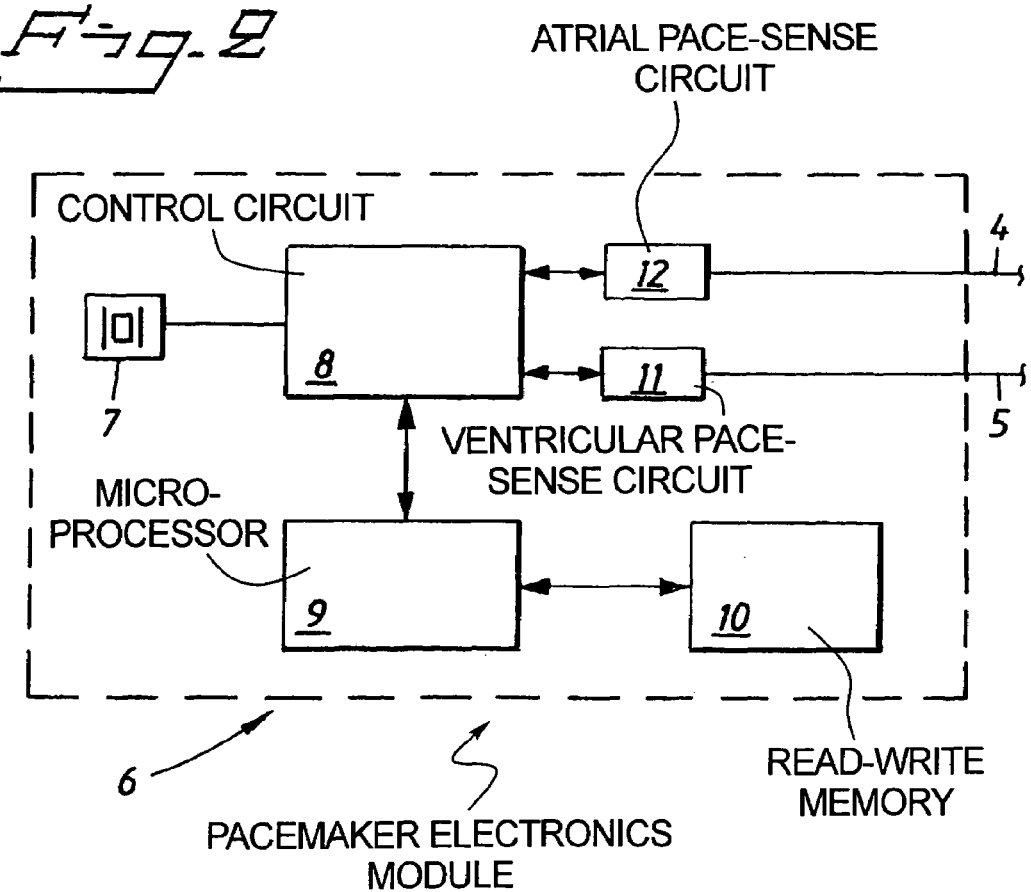
FIG. 2 shows a typical electronics module for a cardiac pacemaker.

FIG. 2 shows a typical design of a pacemaker electronics module 6. The electronics module 6 contains the following elements: micro-processor 9, read-write memory 10, control circuit 8, rate responsive sensor 7, atrial pace-sense circuit 12 and ventricular pace-sense circuit 11. The rate responsive sensor may be either of a physiological type such as a respiration minute volume sensor or of an activity kind such as an accelerometer for measurement of body movements. The microprocessor 9 supervises the operation of the control circuit 8 through execution of code stored in the read-write memory 10. Thus, application-specific algorithms such as control of the AV-interval's dependence on stimulation rate is defined as a software routine in the read-write memory 10.

Figure 3:
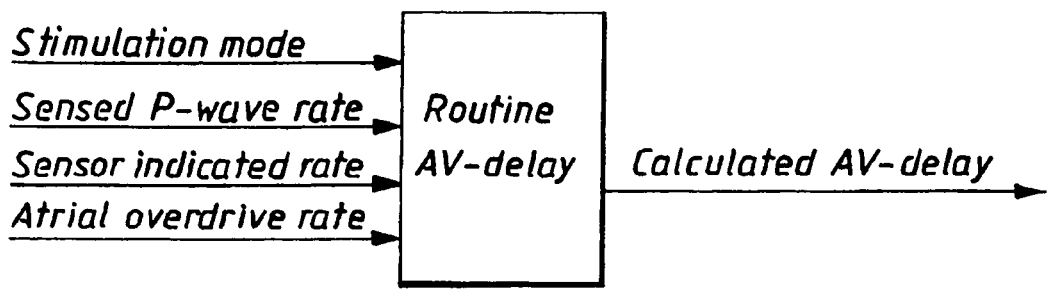
FIG. 3 indicates how the AV delay is determined in a pacemaker according to the invention.

FIG. 3 shows input data that may be used by the AV-delay routine to calculate the AV-delay. Examples of the stimulation mode are atrial overdrive, sensed and tracked P-waves, sensor controlled AV sequential stimulation. The AV-delay is calculated for each heart cycle dependent on stimulation rate and stimulation mode.

Figure 4:
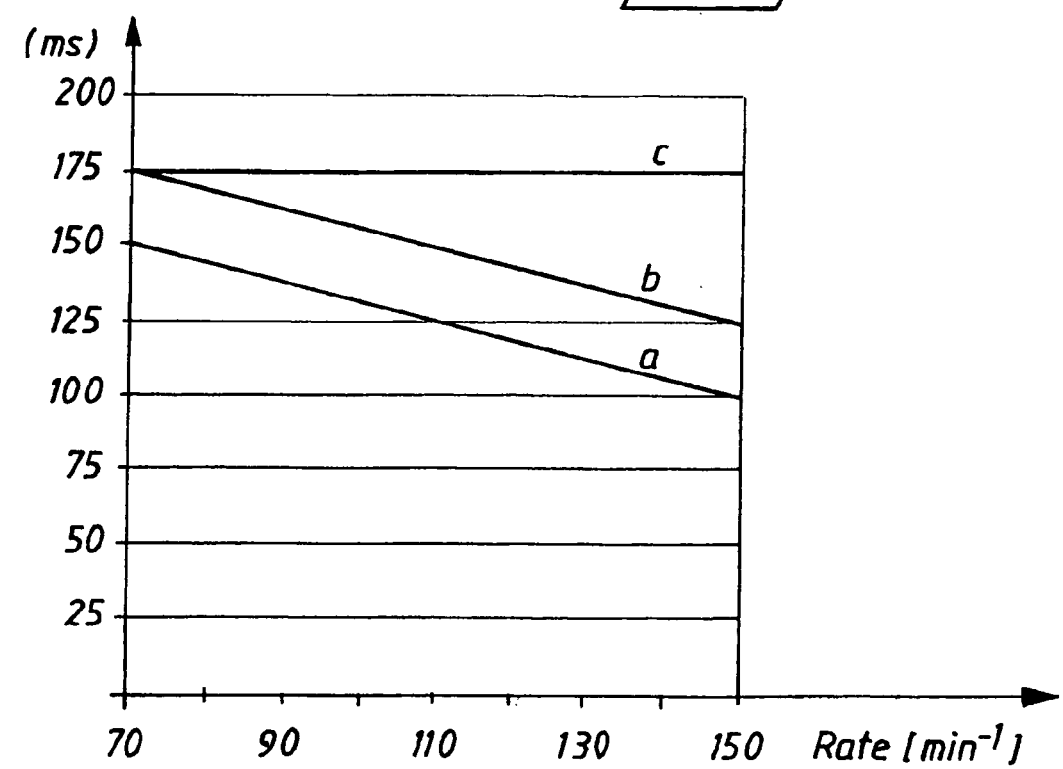
FIG. 4 shows the resulting determined AV delay for different stimulation modes and stimulation rates.

FIG. 4 graphically shows examples of how the AV-delay can be varied dependent on stimulation mode.

Curve a) shows an example of shortening the PV-delay with increasing rate of the sensed P-waves.

Curve b) shows an example of shortening the AV-delay with increasing stimulating rate.

Curve c) shows an example in which the AV delay is held constant independent of stimulating rate during atrial overdrive pacing.

FIG. 5 shows a flowchart of the AV interval calculation. The assumption is that overdrive pacing is activated. First it is determined if overdrive pacing was active during at the last atrial event. If that was the case then provisional AV-delays are calculated according to different calculation rules.

The first input data to be used would be the activity or physiologic sensor indicated rate for determination of an appropriate AV-delay.

The second input data to be used would be the sensed P-wave rate for determination of the AV delay. This will require filtering and averaging since if atrial overdrive is active then only few P-waves will be sensed. The use of filtered and averaged P-wave rate is particularly suitable if the frequency of PAC's is relatively low since in this case the sensed P-wave rate will be physiologically correct. It should be noted, however, that the frequency of sensed atrial events will be less than one atrial event out of 20 so the adaption to changes in physical activity will be poor if sensed P-waves are used alone for AV interval determination. One method for filtering is to use the average interval of the last three sensed P-waves to determine the P-wave rate that will control the AV interval. The third input data to be used would be the actual overdrive rate. It should be noted that the AV interval shortening with increased overdrive will be lower than for sensed P-waves and that the shortening with increasing overdrive rate also may be zero. After having determined the AV interval according to those three criteria the shortest of the three calculated AV intervals are used.

If overdrive pacing was not active at the last event which means that the last atrial event was either a paced event at a rate determined by the rate responsive pacing algorithm or a sensed P-wave the AV interval shall be calculated in a normal manner depending on the paced or sensed heart rate.

The resulting AV interval is written to the control circuit to make the AV interval applicable during the ongoing heart cycle.

There are several other preferred embodiments for determination of the AV-interval during dynamic overdrive pacing. The actually used AV interval during overdrive may be based on only the sensor indicated rate or the AV interval may be determined as a blend from the sensor indicated rate, the sensed and filtered P-wave rate and the actual overdrive rate. One embodiment that may be advantageous for certain patients is to use the base rate AV interval always when atrial pacing pulses are delivered regardless of rate.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable cardiac stimulator comprising:

a housing adapted for implantation in a subject;

an atrial lead adapted for interaction with an atrium of the subject;

a ventricular lead adapted for interaction with a ventricle of said subject;

stimulating pulse generating circuitry in said housing, connected to said atrial lead and to said ventricular lead, for generating stimulating pulses which are conveyed to the atrium and the ventricle, respectively, via said atrial lead and said ventricular lead;

sensing circuitry in said housing connected to said atrial lead and to said ventricular lead for sensing depolarizations in the atrium and the ventricle via said atrial lead and said ventricular lead, respectively;

a control circuit connected to said stimulating pulse generating circuitry and to said sensing circuitry for adjusting sensed and stimulated AV/PV delays and for operating said stimulating pulse generating circuitry to produce physiologically optimal AV/PV delays at different paced and sensed heart rates; and said control circuit operating said stimulating pulse generating circuitry in a mode for dynamic overdrive of the atrium upon a sensing of a predetermined atrial condition by said sensing circuitry and for limiting shortening of the AV delay only when operating said stimulating pulse generating circuitry in said mode.

2. An implantable cardiac stimulator as claimed in claim 1 wherein said control circuit limits shortening of said AV delay during said mode compared to an shortening of said AV delay during AV sequential pacing.

3. An implantable cardiac stimulator as claimed in claim 1 wherein said control circuit limits shortening of said AV delay during said mode by setting said AV delay to be equal to a base rate AV delay.

4. An implantable cardiac stimulator as claimed in claim 1 wherein said control circuit limits shortening of said AV delay during said mode by setting said AV delay to be equal to an AV delay indicated by a depolarization rate sensed by said detector circuitry.

5. An implantable cardiac stimulator as claimed in claim 1 wherein said control circuit limits shortening of said AV delay during said mode to an AV delay indicated by a physiologic underlying intrinsic heart rate.

6. An implantable cardiac stimulator as claimed in claim 1 wherein said control circuit limits shortening of said AV delay during said mode to an AV delay set by a blending of a sensor indicated rate, an actual P-wave rate and an actual overdrive rate.

7. An implantable cardiac stimulator as claimed in claim 1 wherein said control circuit limits shortening of said AV delay during said mode by setting said AV delay to a base rate AV interval independent of pacing rate.

8. An implantable cardiac stimulator as claimed in claim 7 wherein said control circuit also limits shortening of said AV delay by setting said AV delay to said base rate AV interval independent of pacing rate, when not operating said stimulating pulse generating circuitry in said mode.

* * * * *